United States Patent [19]

Baldwin

[11] Patent Number: 4,863,429
[45] Date of Patent: Sep. 5, 1989

[54] SYRINGE DRIVER/SYRINGE/TUBE CONNECTING SET FLUID DELIVERY ARRANGEMENT, AND TUBE CONNECTING SETS THEREFOR

[76] Inventor: Brian E. Baldwin, 8022 South Niagara Way, Englewood, Colo. 80112

[21] Appl. No.: 69,016

[22] Filed: Jun. 30, 1987

[51] Int. Cl.$^4$ .............................................. A61M 37/00
[52] U.S. Cl. ..................... 604/135; 604/246; 138/137; 141/31
[58] Field of Search ............... 604/134, 135, 151, 154, 604/246, 264, 280, 281, 282, 207; 138/137; 141/31

[56] References Cited

U.S. PATENT DOCUMENTS

| | | | |
|---|---|---|---|
| 2,112,737 | 3/1938 | Dodge | 138/137 |
| 2,583,298 | 1/1952 | Kowan | 604/282 |
| 3,115,164 | 12/1963 | Vanderbilt | 138/137 |
| 3,261,356 | 7/1966 | Wallace | 604/264 |
| 3,695,921 | 10/1972 | Shepherd et al. | 604/280 |
| 3,924,632 | 12/1975 | Cook | 604/282 |
| 4,035,534 | 7/1977 | Nyberg | 138/137 |
| 4,202,333 | 5/1980 | Thill et al. | 604/135 |
| 4,211,741 | 7/1980 | Ostoich | 138/137 |
| 4,298,000 | 11/1981 | Thill et al. | 604/135 |
| 4,381,006 | 4/1983 | Genese | 604/135 |
| 4,430,079 | 2/1984 | Thill et al. | 604/154 |
| 4,525,167 | 6/1985 | Goldberg et al. | 604/135 |
| 4,577,543 | 3/1986 | Wilson | 604/282 |
| 4,597,754 | 7/1986 | Thill et al. | 604/135 |
| 4,627,844 | 12/1986 | Schmitt | 138/137 |
| 4,648,870 | 3/1987 | Goldberg et al. | 604/135 |
| 4,681,566 | 7/1987 | Fenton, Jr. et al. | 604/135 |
| 4,723,947 | 2/1988 | Konopka | 604/282 |
| 4,755,172 | 7/1988 | Baldwin | 604/131 |

FOREIGN PATENT DOCUMENTS 2811278 9/1979 Fed. Rep. of Germany ...... 604/280

Primary Examiner—Stephen C. Pellegrino
Assistant Examiner—Ralph Lewis
Attorney, Agent, or Firm—Reginald F. Pippin, Jr.

[57] ABSTRACT

A syringe infusion or other patient health care fluid delivery arrangement or system having a substantially constant force syringe holder/driver for a fluid-dispensing, preferably disposable, syringe to which an on-off valve and effectively bendably flexible tube connecting set are connected. The outside diameter of the tubing of an available flow-rate assortment of suitably identifiably marked tube connecting sets is formed of a desired single size by extrusion addition of a plastic outer overcoat layer over the inner fluid-carrying tubing, enabling interchangeable accommodation and securing thereon of standard single-size conventional or other desired connectors, whereby a single health care professional may fill a syringe with a prescribed dosage and concentration of health care fluid, and may also preselect and fix the delivery rate for the fluid, by selecting and assembling a given syringe holder/driver, fluid-filled syringe and tube connecting set. The syringe holder/driver is powered by a pair of Neg'ator constant force springs which roll off and onto ball-bearing-mounted rotatable drums carried by a syringe plunger pusher or driver which is centered and guided in its longitudinal movement by the opposed Neg'ator springs and the syringe plunger, which springs are laterally stabilized by nonsliding strip-laying stabilizing retentive engagement with, and strip-pickup removal from engagement with, the syringe holder/driver cover.

14 Claims, 2 Drawing Sheets

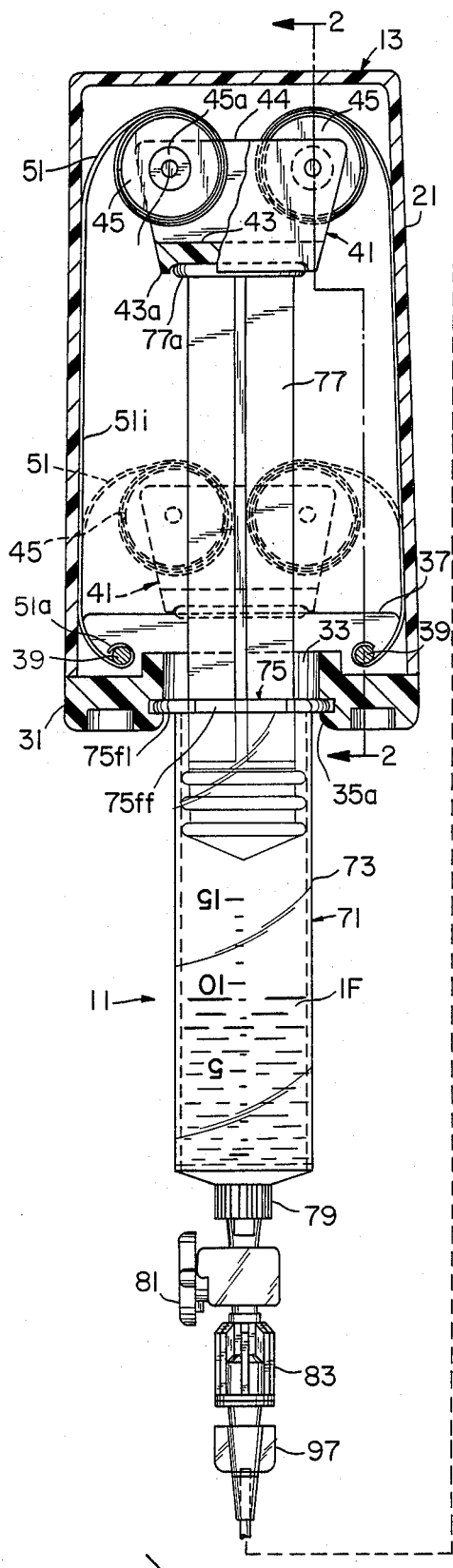
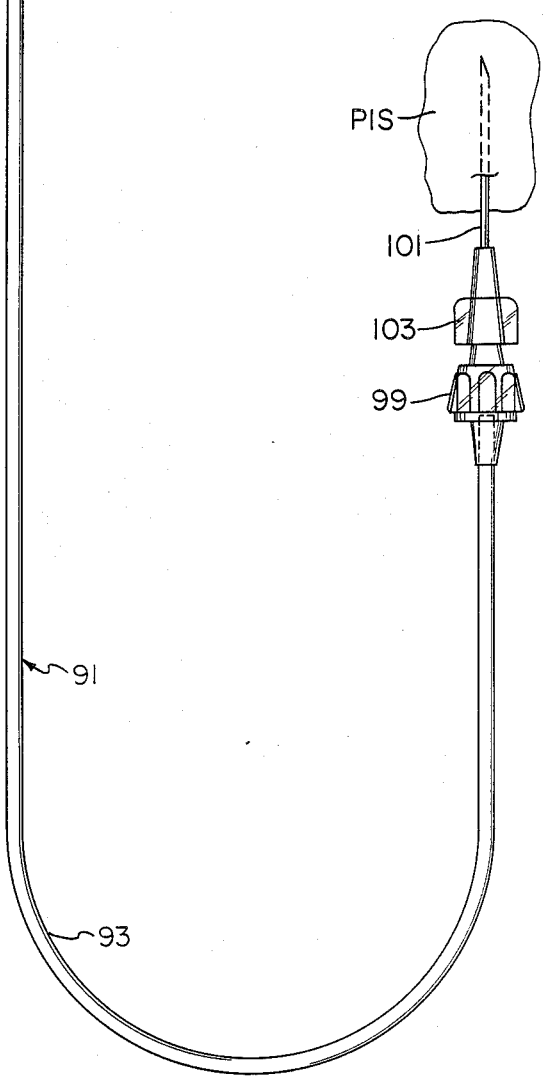
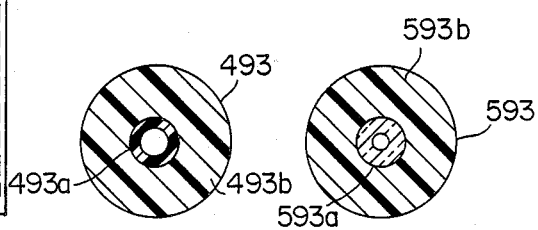
FIG. 1
FIG. 8  FIG. 9

SYRINGE DRIVER/SYRINGE/TUBE CONNECTING SET FLUID DELIVERY ARRANGEMENT, AND TUBE CONNECTING SETS THEREFOR

This invention relates to a syringe driver/syringe/tube connecting set fluid delivery arrangement, and tube-connecting sets for the continuous steady-rate infusion of intravenous fluids or enteral nutrition fluids to a patient, and for other health care fluid delivery requirements in medical or other health care treatment procedures, and more particularly which enables the provision of ambulatory fluid infusion devices of simple construction which provide a high degree of reliability and simplicity in utilization, as well as enabling the use of low-cost standard disposable syringe with a selected unique fixed flow rate self-metering tube connecting set coupled to a reusable compact nonelectrical substantially constant force-applying syringe holder and plunger driver.

In the prior art, one common practice has utilized gravity feed systems in which the feed rate is adjusted by manual setting of adjustable pinch clamps on the connecting tube. Adjustable valves built into the connecting tubes have also been used to selectively control the feed rate. Such systems generally have included a fluid container, a means of generating a pressure differential between the fluid container and the injection site, and a connecting tube between the fluid container and the injection site. The flow rate of the manually adjusted valve sets is observed by an in-line drip chamber where drops are counted manually over a measured time period. This system and method are prone to error due to such factors as drop size variations with fluids having different characteristics, including variations in surface tension.

Various electronic control systems have recently been provided, utilizing drop counters and microprocessor feedback systems which electronically regulate a flow control system.

In a further advance, accuracy was improved through use of a piston chamber and piston, with precise mechanical reciprocation of the piston, in lieu of drop counting. This latter type of system is known as a pump, and delivers fluids under certain pump pressure. This type of system poses a hazard in the event of occlusion. Various complicating additional mechanisms, such as pressure-sensing protectors or pressure relief systems, have been utilized to alleviate or minimize this hazard.

In further prior art systems, syringes are used for continuous rate fluid delivery, utilizing electrochemical plunger driving systems in which the feed rate is adjustable as well as preset.

Ambulatory infusion is often desirable for patients who require precise continuous feed-rate medication delivery but are otherwise not bedridden. Various miniature battery-powered syringe pumps or small battery-powered piston or peristaltic pumps have been used for this purpose. Versions of such arrangements have been implanted in the body where long-term use is expected, with a subcutaneous port implanted to enable refilling of the drug reservoir.

In another type of ambulatory system, fluid feed pressure is achieved by use of a rubber tube or bladder inflated with the fluid to be delivered to the patient. In this system (such as shown in U.S. Pat. Nos. 4,318,400, 3,895,631, 3,993,069, 4,140,117 and 4,201,207) the fluid flow rate is controlled by a short rigid glass capillary flow restrictor which is sized to provide the desired flow rate when the fluid is at a constant predetermined pressure based on the theoretically predictable elasticity of the rubber forming the rubber tube or bladder. The short length of glass capillary is preceded in the fluid path by a filter to prevent particles in the fluid from plugging the very small orifice. The flexible fluid-connecting tube is much larger than the orifice in the short rigid glass capillary and essentially serves as simply a fluid conduit, the fluid flow metering through the connecting tube being effected by the short rigid capillary and accompanying filter, the latter of which may vary in flow restriction as it filters out particles and becomes more restrictive to flow therethrough. This entire device is used only one time and discarded.

In U.S. Pat. No. 4,298,000 to Thill, assigned to Minnesota Mining and Manufacturing Co. (3M), a single constant-force spring, known and commercially available under the trademark "Neg'ator," is utilized. Guidance for the spring is provided by a slide system. The constant spring force is applied to a syringe plunger to effect fluid pressure in the system. However, as there is considerable friction in the reusable slide, as well as in the syringe plunger, the necessary spring force is quite high, and a mechanical toggle-type lever is used to apply the spring force after the syringe is in place. Because of the large forces, the device is inherently large, and is therefore unsuitable for ambulatory infusion. The flow-rate in this system is fixed by the selection of a short plastic capillary tube inserted within the fluid pathway of a larger tube. In order to purge the air from the larger long connecting tube, a two-position bypass valve is included which enables the user to switch from the slow controlled flow through the capillary to the higher purge flow-rate bypassing the capillary. The small diameter of the capillary also requires the use of a filter upstream from the capillary.

A similar syringe infusion device which is driven by a pair of Neg'ator springs is disclosed in U.S. Pat. No. 4,381,006. In this patent, which was granted in 1983 and assigned to Abbott Laboratories, two Neg'ator springs drive a syringe plunger, with relative sliding motion of the plunger and the motion-imparting element being guided by two slide rods. In this system the syringe constant fluid pressure system is coupled to the injection site with a connecting tube which contains a variable flow restrictor of the needle valve type.

In U.S. Pat. Nos. 4,557,728 and 4,447,232 to Sealfon, two Neg'ator springs are employed to apply pressure to a collapsible bag. The springs drive a box-like member which slides inside an outer box. No flow control system is described for use in association with the device.

U.S. Pat. No. 3,670,926 to Hill discloses a slide guide system and a single Neg'ator coil spring to compress a fluid bag. This arrangement would not appear to provide constant pressure. There is reference to a manually operated pinch clamp to control flow.

In U.S. Pat. No. 3,647,117 to Hargest, a single Neg'ator constant force spring compreses a bag to provide fluid delivery force. In an optical arrangement, the coil spring appears to drive a syringe plunger. It appears that there would be a problem in use of this arrangement due to the frictional force of the rotating coil spring applying a lateral force on the syringe plunger and causing binding or excessive friction. This device also uses sliding guide rails.

The extensive amount of prior patent art employing some means of providing a constant pressure fluid container (other than a gravity-fed bottle) coupled to some flow control system capable of very slow flow-rates is testimony to the long-felt need for a low-cost, compact, ambulatory intravenous drug administration system. The only devices of which I am aware of having reached the market are the Thill device (U.S. Pat. No. 4,298,000 marketed by 3M) which is too large for ambulatory care, and a device of the type shown by Peery et al and Buckles et al patents (U.S. Pat. Nos. 4,318,400 and 3,895,631, respectively, marketed by Travenol) using inflated rubber fluid containers. To my knowledge, none of the others have formed a useful commercial product. The Thill (3M) device has had very limited marketing and, at one point, was taken off the market. It has reentered the market in the last year, but has still not received much acceptance due to its size.

The Travenol inflated rubber container device is receiving much acceptance in critical chemotherapy drug administration, where it is being sold as a "24-hour infusor" in which drug is delivered at the rate of 2 ml per hour. This product depends for flow-rate accuracy on constant pressure developed by the inflated rubber tube or bladder. There are inherent problems with getting this pressure to be uniform from one device to the next. It appears that there are a great many variables in the production process of the rubber tube or bladder, as well as elasticity changes due to age, heat, etc. The units are packaged in an expensive aluminum-foil-sealed pouch to protect from exposure to oxygen or light, both having deleterious effects on the rubber. The labeling of the units does not specify an accuracy tolerance. However, in prior art U.S. Pat. No. 3,993,069 (Column 3, Lines 12-16) it is stated that "If the pressure variation from the mean is more than ten percent (10%), it is not possible to obtain the constant rates of delivery of liquid from the devices which are required by the present invention."

Another problem with the Travenol unit as marketed is the inability to eliminate all air bubbles after filling. While there is a description of a method for removing the air in U.S. Pat. No. 4,318,400 (Column 4, lines 16-24), the air vent described in the patent and shown in the Drawings (64) does not exist in the device as now marketed. Instead, there is a note in the labeling that "The pea-sized bubble of air within the balloon reservoir is normal." However, in the view of the user community, there is certainly a perceived, if not actual, hazard of air in intravenous delivery lines.

A further problem with the Travenol unit is the time required to fill and inflate the rubber balloon container with the drug. It requires up to one minute to fill, due to the limited flow-rate through a 22- to 20-gauge needle which enters the fluid cavity through a rubber septum.

Another important problem with the Travenol unit is the length of time it takes to purge the air from the tube set, which is up to three (3) minutes. This is due to the short glass orifice flow restrictor built into the unit, followed by the flexible plastic tube set which is 36 inches long and has a volume of approximately 0.1 ml.

Time is a valuable commodity for pharmacists, doctors and nurses who are preparing these devices. The need for rapid purging of air is evident from the above-described Thill (3M) device in which there is a two-position valve provided, one position being for capillary tube bypass to enable rapid air purge, and the other position being for normal flow through the capillary tube flow restriction section for fixed-rate flow control.

In all of the devices in the prior art in which very low flow-rates are provided, either a single very small orifice flow-rate restrictor or a flow-rate restrictor having a multiplicity of minute pores is incorporated. Because of the very small openings in the flow-rate restrictor, there is a need for a filter upstream from the flow restrictor to prevent particles from plugging up the flow restrictor. All medicaments are likely to contain microparticles. The single large flow restrictor is less likely to encounter a particle large enough to totally stop flow. However, while the multiple pore-flow restrictors will not normally plug completely as particles are lodged in the pore openings during the course of the drug delivery, any particles not passing through will cause an undesired and unpredictable reduction of flow rate. The single larger flow restrictor as used in the 3M and Travenol units is protected from plugging by having a filter upstream. This filter is, of course, also a flow restrictor, so any significant plugging of the filter will also reduce the flow-rate of the system.

All of the prior art devices have accomplished the flow-rate control with very expensive high precision flow restriction orifices and filter elements. They also must overcome the air purge problem with a bypass valve arrangement, as in the Thill (3M) unit, or suffer with the slow air purge as in the case of Travenol unit.

Genese U.S. Pat. No. 4,381,006 (assigned to Abbott Laboratories) incorporates a pair of Neg'ator springs, as does the Sealfon U.S. Pat. No. 4,557,728 (assigned to Repro-Med Systems, Inc.) Both of these devices have slide members which serve as guides for the linear movement of the plunger. The use of the slide members in a reusable device presents a reliability problem in that, over a period of time, there is unpredictable friction in the system. As the friction force must be subtracted from the spring force to obtain the net force used to develop the constant pressure in the fluid, any change in the friction will change the pressure and, thus, the flow rate. Any friction-bearing system employed over time will introduce a variable which can change flow-rate and is certainly unpredictable.

In the case of the Abbot device (U.S. Pat. No. 4,381,006) a syringe is used which in itself has a friction force which can vary. This variable can be managed since the variable can be predetermined to an acceptable level of confidence by statistical analysis of the measurement of the friction forces in a large sample of the syringes to be used. However, the friction forces in the reusable spring-and-slide device can vary substantially as the devices are used, due to dirt particles, fluids, corrosion, etc.

The Thill (3M) device uses a single reusable Neg'ator spring system which necessarily has a guide system with variable friction. This is accommodated by using a quite large spring force of a sufficiently large value that variations in the slide friction will be a small percentage of the total force applied. This Thill (3M) system thus requires more force be applied than a person can be expected to apply directly. To accommodate this requirement, the Thill (3M) device is made with a large lever arrangement to give a mechanical advantage in loading the syringe into the spring force system. This is a large and heavy system which renders it substantially unusable for ambulatory care.

Cost, simplicity, ease of ambulatory portability and use, accuracy and reliability are all important factors in the acceptability and use of a given infusion or other health care fluid delivery system and components and methods of manufacture and use thereof, and the prior art systems and methods all suffer from one or more deficiencies in these and other aspects.

It is an object of this invention to provide a low-cost, compact fluid delivery system which enables the administration of fluids to a patient at a slow predetermined fixed rate which the patient cannot change, and which can be readily administered while the patient is ambulatory.

It is a further object of the invention to provide a fluid delivery system in which the contents of a fluid dispensing syringe, as well as the flow rate therefrom, can be fixed by a pharmacist or other single health care professional, whereby responsibility for correct drug administration can be personally focused as to both drug concentration and rate of delivery.

A further object of the invention is the provision of a more accurate health care fluid delivery system having less chance of variations in flow rate than that of prior art devices where flow is controlled by a constant pressure device coupled to a flow restrictor.

It is also an object to provide a health care fluid delivery system enabling a fixed preset substantially constant slow rate of fluid delivery to a patient, yet which enables the relatively rapid purging of air from the fluid path without the use of fluid bypass systems which would add cost and complexity as has occurred with various prior art systems.

Another object of the invention is to provide a fluid delivery system employing a simple substantially constant force syringe holder/driver, syringe and tube connecting set and in which essentially the only material mechanical movement friction losses are those resulting from the inherent friction encountered in sliding movement of a plunger in the barrel of the syringe.

A further object of the invention is to provide a flexible tube-connecting set which serves the dual functions of effecting fluid delivery through a bendably flexible path, and self-metering of fluid flow therethrough, while providing a maximum diameter flow pathway which will still provide necessary flow rate control.

It is also an object and feature to provide a substantially constant-force-applying and substantially constant flow rate health care fluid delivery system enabling utilization of a low-pressure spring-loaded system, whereby any occlusion of the fluid administration path would not produce a hazardous condition.

Still a further object and feature of the invention is the provision of dual function fluid delivery and self-metering fixed flow rate tube connecting sets.

Still other objects, features and attendant advantages will become apparent from a reading of the following detailed description of the invention in its various aspects, taken in conjunction with the accompanying drawings wherein:

FIG. 1 is an overall view, partially cut away for ease of illustration, of a syringe infusion arrangement according to the invention.

Figure 4:
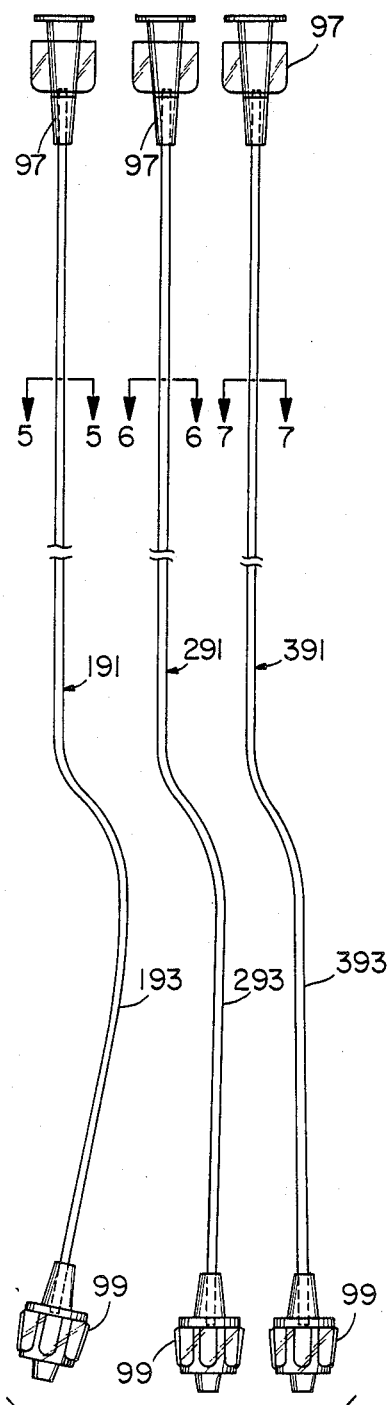
FIG. 4 illustrates an assortment of several interchangeably interconnectable tube-connecting sets constructed according to one aspect of my invention.
Figure 3:
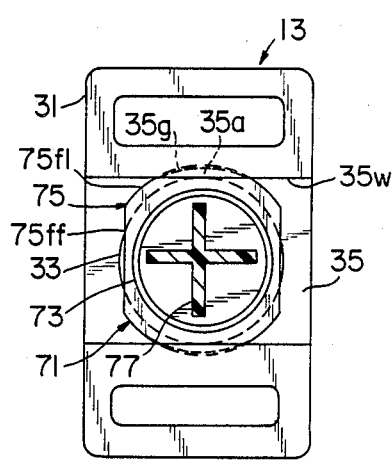
FIG. 3 is a section view taken on line 3—3 of FIG. 2.
Figure 2:
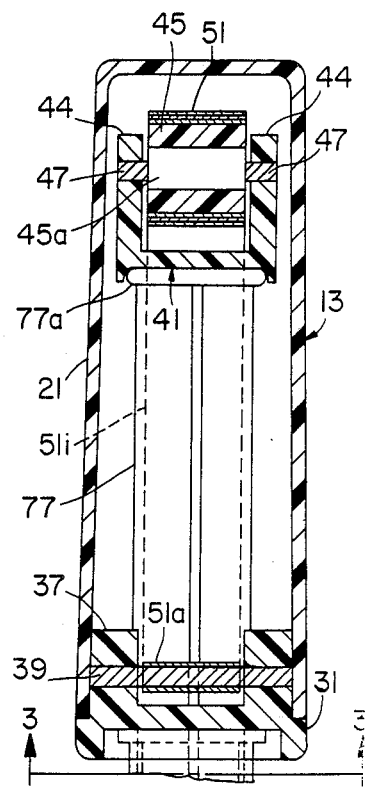
FIG. 2 is a section view taken on line 2—2 of FIG. 1.
Figure 5:
Figure 6:
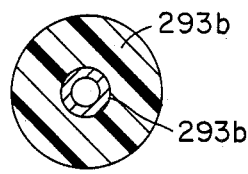
Figure 7:
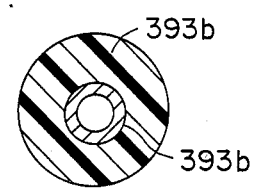

FIGS. 5, 6 and 7 are enlarged section views taken respectively on lines 5—5, 6—6 and 7—7 of FIG. 4.

FIGS. 8 and 9 are section views similar to FIGS. 5-7, showing modified tube-connecting set constructions employing respectively plastic and glass inner tubing according to one aspect of my invention.

Figure 10:
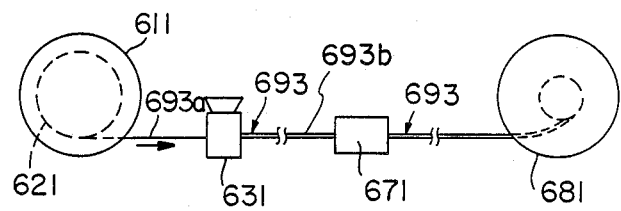

FIG. 10 is a schematic illustration of the extrusion coating of sized tubing according to one aspect of my invention.

Referring now in detail to the Figures of the drawing, a metered fluid delivery syringe infusion assembly or arrangement 11 is provided, which includes a force-applying syringe holder/driver 13, to which a standard plastic syringe 71 may be suitably releasably secured for delivery of a suitable desired fluid to a patient infusion site PIS through an effectively bendably flexible tube-connecting set 91, having a fluid delivery needle 101 secured thereto as by a Luer-type connector 103, removably attached to a complementary Luer connector 99 on the end of tube connecting set 91. On-off flow control may be accomplished with a simple conventional on-off cut-off valve 81, which may be removably connected between the discharge end connector 79 formed on the fluid discharge or exit end of the barrel 73 of syringe 71, and the Luer connector 97 on the entrance end of the tube-connecting set 91.

Syringe holder/driver 13 includes a cover 21 which encloses a dual spring-driving assembly including a pair of oppositely outwardly convexly bowed Neg'ator constant-force coiled strip springs 51 which are wound about and are self-rolled onto and off of respective drums 45 mounted in parallel-spaced relation on a longitudinally freely movable plunger/pusher or driver 41.

Springs 51 may be suitably self-secured onto the drums 45 as by multiple wraps thereabout, or may be otherwise suitably secured thereto at their ends if so desired. At their respective opposite ends 51a, springs 51 may be suitably crimped and secured about respective anchor pins 39 press-fit into upstanding parallel anchor shoulders 37 on an anchor/securing block 31, between which anchor shoulders 37 the springs 51 extend in substantially laterally centered relation, front-to-back as viewed in FIG. 1.

Drums 45 are each mounted on ball bearings 45a to minimize frictional resistance to rolling and unrolling of the springs 51 onto and from their respective drums 45, each of the bearings 45a being in turn mounted on a respective one of two spaced parallel axle or support pins 47 which are press-fit into upstanding parallel-spaced drum support shoulders 44 extending in close relation on either side of the drums 45, from a transverse pusher or driver seat 43.

Anchor/securing block 31 has a central circular mouth 33 formed therein, which accepts and accommodates the entrance and exit of plunger 77 therethrough for syringe-loading of the holder/driver 13.

Pusher or driver seat 43 has an annular peripheral lip 43a which complements flanged end 77a of plunger 77 and centers and aligns the plunger pusher or driver 41 with the finger-gripping flanged end 77a of syringe plunger 77, which plunger 77 and syringe barrel 73 is in turn substantially centered relative to mouth 33 of the anchor/securing block 31.

Anchor/securing block 31 also has formed on its lower (as viewed in FIG. 1) exterior face a front-to-rear transverse end face slot 35 connecting with the circular mouth 33 and which has a transverse slot width sufficient to accommodate the transverse distance between opposed parallel flaconventional finger-grip flange 75 of syringe barrel 73, the end face slot 35 being of lesser width than the oppositely extending radially extended round flange lip portions 75fl of the flange 75. Transversely concave grooves 35g are formed in the opposite parallel side walls 35w of end face slot 35 of a size to complementarily receive and retain opposed radially extended round flange lip portions 75fl when the syringe barrel flange 75 is inserted into slot 35 and rotated 90°. Groove 35g and associated retention lips 35a forming a lower wall of groove 35g thus retain the lip portions 75fl of barrel flange 75 in thus 90° rotated position of the syringe barrel 73 and thereby hold the distended syringe 71 centrally of and with its plunger 75 extending within central mouth 33 of the syringe holder/driver 13.

In the quiescent state of syringe holder/driver 13 prior to loading a syringe therein, the springs 51 are rolled into retracted wound condition onto their respective drums 45, and the plunger/pusher or driver 41 is thereby pulled down and resiliently held by springs 51 in centrally seated position against the top edge surfaces of anchor/securing block shoulders 37, as shown in phantom lines in FIG. 1. In this position, the springs 51 bow outwardly and engage the adjacent opposite inner walls of cover 21 over a relatively short extent.

The syringe 71 as shown in fluid-filled and assembled loaded condition in FIG. 1 is loaded into the holder/driver 13 after first filling the syringe with a desired quantity of a fluid IF desired to be administered to a patient, and closing the valve 81 to "off" position to prevent escape of fluid from the syringe 71 during loading of the syringe 71 into holder/driver 13 and prior to desired fluid expulsion from the syringe 71.

The syringe plunger 77 will be extended to the extent of its partial or fully filled condition, and the thus-extended plunger is inserted through mouth 33 into centered engagement with the plunger/pusher or driver 41. Syringe barrel 73 is pushed upwardly to thereby push plunger 77 and plunger/pusher or driver 41 upwardly away from anchor/securing block 31, until the finger grip flange 75 of syringe barrel 73 seats against the recessed flat base of end face slot 35 in anchor/securing block 31, with the opposing parallel flats 75ff of flange 75 parallel to the side walls 35w of end face slot 35. Thereupon, the barrel 73 is rotated 90° to engage the flange lips 75fl in the complementary concave grooves 35g.

In this loaded assembly of syringe 71 with syringe holder/driver 13, the plunger/pusher or driver 41 will be held away from the anchor/securing block 31 by the extended syringe plunger 77, and the oppositely outwardly bowed Neg'ator constant force strip springs 51 will be extended from their rolled-up position and will lay generally against the respective opposite inner sidewalls of cover 21 as indicated at 51a, although extended distention of spring 51 may pull the spring sufficient taut to cause the substantial extent of spring length 51a to be spaced inwardly away from the adjacent wall of cover 21. The thus extended springs exert the desired constant expulsion or driving force on plunger 77 to effect fluid discharge through the effectively bendably flexible tube-connecting set 91 and needle 101 for expiration and subsequent preset metered delivery of fluid IF to a patient.

In the plunger-driving movement of the plunger/pusher or driver 41 by springs 51, it will be seen that the plunger/pusher or driver 41 is free of sliding engagement with the cover 21 or any other part, and the springs 51 roll up onto the negligibly low friction ball bearing mounted drums 45, while simply moving in successive incremental strip-pickup fashion away from the opposite stabilizing and protective walls of cover 21, without any sliding contact therewith. Thus, essentially the only material mechanical friction force acting in the fluid delivery action of the holder/driver 13/syringe 71 assembly is that inherent in the sliding contact discharge movement of plunger 77 along syringe barrel 73. It will be appreciated, of course, that this statement is not intended to refer to absence of fluid flow resistance through the tube connecting set, as such fluid flow resistance on a precision predetermined basis is an important feature of one aspect of the invention.

The syringe 71 may desirably be a standard disposable syringe, the barrel 73 of which may be molded of polypropylene or other suitable plastic material, the molded plastic plunger 77 having a conventional molded rubber end seal which fits snugly in sliding contact within the barrel 73. The plunger 77 is moved longitudinally within the barrel 73 to either aspirate or to inject a fluid solution IF, after filling with fluid IF through the rear of barrel 73. It will be appreciated that a friction force is produced between the wall of barrel 73 and the end seal on plunger 77 by this plunger movement, which friction varies with the size of the syringe.

It is desirable to employ a fluid pressure within the syringe 71 which is not in excess of 650 mmHg, or 12.6 psi. Pressures greater than this could be hazardous if an occlusion should occur in the fluid flow path. In the practice of the present invention, I have found it feasible to maintain a fluid delivery system pressure within a relatively close and acceptable tolerance of a safe 11.5 psi, and to enable provision of syringe fluid delivery arrangements 11 which can be constructed and sized to enable use of all syringe sizes from 3 ml to 60 ml while attaining this fluid delivery system pressure objective. The plunger area of a standard 3 ml syringe is 0.096 square inch, while the area of the standard 60 ml syringe plunger is 0.858 square inch. Accordingly, the force to develop 11.5 psi in the 60 ml syringe is 9.867 pounds, and the force required for the 3 ml syringe is 1.104 pounds.

Standard disposable syringes in the 60 ml size have friction varying from 1.18 pounds to 2.043 pounds, while the 3 ml syringe varies in friction from 0.118 pounds to 0.306 pounds. These syringe forces must be subtracted from the essentially constant-plunger-driving force provided by springs 51 acting through pusher or driver 41, to obtain the net force available to develop the objective 11.5 psi for the fluid delivering system. Table I shows the syringe friction force averages, as well as the minimum and maximum forces and pressures encountered, based on analysis of the range of friction forces for the various standard syringe sizes from 3 ml to 60 ml, which friction forces can be predicted to an acceptable degree of variation.

TABLE 1

| In² Area | Vol ml | Total Spring Force (lb) | Avg. Friction | Avg. Net Force | Min. Friction | Max. Net Force | Max. Friction | Min. Net Force | Avg. psi | Max psi | Min psi | Max Δ% | Min Δ% |
|---|---|---|---|---|---|---|---|---|---|---|---|---|---|
| 0.858 | 60 | 11.567 | 1.700 | 9.867 | 1.180 | 10.387 | 2.043 | 9.524 | 11.5 | 12.106 | 11.100 | +5.3 | −3.5 |
| 0.691 | 35 | 8.320 | 0.373 | 7.947 | 0.313 | 8.007 | 0.431 | 7.889 | 11.5 | 11.588 | 11.417 | +0.8 | −0.7 |
| 0.500 | 20 | 6.145 | 0.395 | 5.750 | 0.312 | 5.833 | 0.490 | 5.655 | 11.5 | 11.666 | 11.310 | +1.44 | −1.7 |
| 0.304 | 12 | 3.937 | 0.441 | 3.496 | 0.271 | 3.666 | 0.584 | 3.353 | 11.5 | 12.059 | 11.030 | +4.9 | −4.1 |
| 0.096 | 3 | 1.309 | 0.205 | 1.104 | 0.118 | 1.191 | 0.306 | 1.003 | 11.5 | 12.406 | 10.448 | +7.9 | −9.1 |

It will be appreciated that the syringe 71 and syringe holder/driver 13 arrangement according to the present invention, and as shown illustratively in FIG. 1, enable the employment of low forces and pressures where the friction range of the syringe plunger 77 is small in relationship to the force used to achieve the pressure. If more friction variation were introduced into the system by the use of any sliding guide system for the syringe holder/driver 13, as has been present with various prior art systems, it would be necessary to use high forces and pressure to stay within the ±10 percent variation limit, which would introduce a hazardous condition in the event of occlusion of the fluid path, as well as creating a materially larger mechanical syringe driver arrangement which would be both heavier and require more syringe-loading force, and also rendering the arrangement nonambulatory, as is the case with the previously discussed 3M unit.

The tube connecting set 91 has conventional Luer connectors 97, 99 secured onto opposite ends of flexible tube 93, and is removably locked in fluid delivery connection with the syringe 71 by conventionally removably locked engagement with a complementary connector 83 on intermediate connecting on-off cut-off valve 81 in the illustrative example.

Tube connecting set 91 serves the dual function of providing an effectively bendably flexible fluid conduit for suitable manipulation and connection to a patient infusion site PIS or other patient fluid delivery site, as well as serving as a preselectable predetermined fixed metered flow rate control means for precise preset controlled delivery of fluid IF to a patient. To this end, the tube 93 is constructed to be effectively bendably flexible and its inside flow path diameter along its entire length is essentially uniform, being sized in both ID and length to accomplish the necessary flow restriction for the given pressure so as to achieve the desired flow rate. As used herein, the term "effectively bendably flexible" is employed to refer to the practically necessary flexibility required for conventional health care use in connecting a separate syringe, such as employed in the present invention, to a patient delivery site such as a patient infusion site PIS, and it has been found in practice that such necessitates the ability to bend through an arc of as small as approximately three-inch radius without taking a set. This may be acceptably accomplished according to this invention, as will be described further along.

According to one practical example, the tube connecting sets 91 are nominally 36 inches in length; however, variations of six inches either way are acceptable and usable under health care practice. Flow rates which are conventionally desired may range from 0.1 ml per hour to as much as 100 ml per hour.

Since there is a necessary variation in pressure due to the friction variations of the syringes 71, it is critical that the flow restriction provided by the tube connecting sets 91 be very accurate if the total tolerance for flow delivery rate to a patient is to be maintained within ±10 percent.

The inside diameter ID of a 36-inch-long tube having a flow rate 0.1 ml/hour, with a pressure drop of 11.5 psi, is theoretically approximately 80.39 uM. Calculation of this approximate ID is based on the well-known Poiseuille's Law, expressed in simplified form by the equation:

$$Q = \frac{P\pi r^4}{8ln}$$

where Q is the flow rate in ml/sec, P is the pressure drop in the tube in dynes per square cm, r is the internal radius in cm, l is the length of the tube in cm, and n is the liquid viscosity in poise, and in which the fluid flow is assumed to be laminar and steady through a length of straight circular tubing of constant diameter. In the above calculation of flow rate, the liquid is assumed to be water at 20° C., with a viscosity of 0.01005 poise. It will be appreciated that, in actual practice, the health care fluid to be administered will usually be more viscous, producing a flow rate of the order of about ten percent slower, thus requiring appropriate adjustment of inside diameters employed for various fluids IF being employed, and such conversion may be readily accomplished. For purposes of simplicity of discussion herein, the calculations assume that the fluid IF is water.

With the variations in inside diameter affecting the flow rate by the fourth power of inside diameter dimension variations, it can be readily recognized that the requirement for a tube connecting set 91 with this design, which is very precise is not practical as an ordinary matter, considering that commercially available tubing made of acceptable materials such as plastic, stainless steel or glass (fused silica) has a tolerance, as commercially supplied, of ±3 uM in the size required for 0.1 ml/hour flow rate, and ±6 uM in the size for 0.2 ml/hour flow rate. This would result in variations of ±15 percent in flow rate, which would result in a total system flow rate variation of up to 25 percent when coupled with the variation caused by the syringe piston friction. This would be totally unacceptable for the intended use of drug fluids administration.

A unique method of achieving very close tolerance flow control in the tube connecting sets is provided, according to one aspect of my invention. By measuring commercially available tubing with commercial tolerances, it has been found that a coil of the tubing produced in a single continuous run is very uniform in dimension throughout the full length of the coil, the end-to-end variation for a 10,000-foot length of stainless steel tubing being normally within three or four percent or less, for plastic tubing within eight or nine percent, and for glass tubing within approximately four or five percent. In the illustrative example of 36-inch nominal length tube 93, samples of a production coil of tubing are taken from both ends of the coil and tested for flow rate using 36-inch-long samples, the test average being taken as the 36-inch-length flow rate.

The variation in flow rate produced by length variation is indirectly proportionate to length according to Poiseuille's Law. If a tested tube at 36-inch length is found to have a flow rate which is ten percent too high, this entire coil is marked to be cut to a length which is ten percent longer, or 39.6 inches. This longer length reduces the flow by ten percent, to thereby effect the desired flow rate through this length of the particular run of tubing.

Referring to FIG. 10, after the tubing 93a (designated in FIG. 10 as 693a) of a particular production run coil 621 has been tested, the entire coil 621 of tubing 693a, which may suitably be on a supply spool or reel 611, is run through an extruder 631 which adds an overcoat or layer of plastic 693b over the original tubing 693a, thereby forming a composite tubing 693 of enlarged outside diameter of, for example, approximately 1/16-inch OD, which is uniform along its length and which uniform enlarged outer diameter is interchangeably employed for all coil ID sizes, thereby enabling the provision of an interchangeably uniform OD, e.g. approximately 1/16 inch, for all tube connecting sets 91, which also enables accommodation and use of standard uniform single size connectors such as Luer-type connectors 97, 99. The plastic extrusion overcoated tubing 693 may subsequently be cured as by passing the overcoated tubing 693 through a suitable curing device 671, after which the cured composite overcoated tubing 693 may be taken up into a take-up reel or spool 681 for subsequent cutting into lengths. This pretested and overcoated tubing is then cut to the specified length for the particular desired flow rate, to obtain tubing lengths which will have precisely the correct flow rate at the desired 11.5 psi pressure. Fittings are affixed to each end, which are standard Luer-type connectors, by use of adhesive, heat or insert plastic molding.

The extruded plastic layer 693b may be distinctively colored, or other indicia my be applied, to indicate the designated flow rate. Since length variations of the tube connecting sets 91 of up to 17 percent or ±6 inches are acceptable in actual use, this method of achieving precise flow rates allows the production of very low-cost metering tube connecting sets 91.

The further advantage of having a tube connecting set in which the entire length is of uniform interior dimension is that there is no need for a method for fast air purging of the line as is the case with prior art devices. The total volume in the tube 93 is so low that the fluid fills the tube in about 20 seconds for the 2.0 ml/hour set, as compared with three minutes for the prior art Travenol unit at the same flow rate. In the Travenol unit there is no bypass to purge the air, and the person doing the filling must wait for the three-minute purge before closing off the end of the tube.

In the practice of this invention there may be situations where tube connecting sets of other nominal lengths are desired. In this situation, flow control tube connecting sets of shorter or longer nominal length could be prepared, using the same method and construction. Also, a metering flow control tube connecting set according to this invention may, if desired, be used in conjunction, such as in tandem or series, with another conventional tube connecting set, such as a tube connecting set of substantially larger effectively nonmetering interior diameter.

By using longer lengths of tube with larger ID's as flow restrictors, the need for a filter upstream in the fluid path to prevent occlusion is largely alleviated, since the long tubing lengths permit using much larger interior diameters for flow restriction. The resultant larger diameter, which may be thus employed while still effecting the desired flow restriction and fixed metered flow rate, is much greater than any likely particle in a medical fluid, and thus need not be protected by an upstream filter. Such a filter in prior art devices is an additional source of variation in flow rate since the pressure drop through a filter may vary due to variables in the manufacture or placement of the filter. The uses of a filter also means that, as the fluid is administered, there is a likely build-up of particles on or in the filter which will cause an increasing pressure drop during the fluid administration which would result in a reduced flow rate as the fluid is given.

For comparison, the Travenol infusor uses a rigid very short capillary (i.e. 4 mm length) with 490 mmHg pressure (9.478 psi). This calculates to require a 45.7 uM (0.0018-inch) inside diameter. The present invention, on the other hand, enables use of a substantially larger ID dual function effectively bendably flexible precision self-metering long tube connecting set 91 of, for example, as much as 42 inches or more in length, and which may also, if desired, be of shorter nominal or actual length such as, for example, three inches, for acceptable flow rates with commercially available effectively flexible bendable tubing having interior diameters which enable metered flow-controlled fluid delivery without necessity for an upstream filter.

Since the inside diameter changes proportionately to the fourth power of the reciprocal of the length according to Poiseulle's Law, there is a very large increase in the tube diameter when going from a short rigid capillary length, as employed in the Travenol infusor, to the lengths employed for practical effectively bendably flexible tube connecting sets 91 as afforded in practice of the present invention. For a typical 2 ml/hour flow rate, the following are the theoretical inside diameters and lengths for effectively bendably flexible tube connecting sets 91 according to this invention, using 11.5 psi fluid pressure (water fluid IF).

| Length (inches) | Inside Diameter (Microns = uM) |
| --- | --- |
| 36 | 170.0 |
| 42 | 176.7 |
| 18 | 143.0 |
| 9 | 120.2 |
| 6 | 108.6 |
| 3 | 91.3 |

For purposes of practice of the invention to achieve the desired effectively flexibly bendable tubing 93 of the tube connecting sets 91, this may be attained with any one of stainless steel, glass or plastic inner tubing 93a (the hundreds prefix numbers 1-6 being added to the original reference numeral 93a (e.g. 193a, 293a, etc.) for the inner tubing simply to designate various illustrative forms or physical embodiments of the tubing 93a, as well as the overcoat layer 93b (e.g. 193b, 293b, etc.), composite tubing 91 (e.g. 191, 291, etc.). The preferred material for the inner tubing 93a is stainless steel, due particularly to the smaller coil end-to-end ID tolerance variations found in production coil runs thereof, although the conventional production runs of plastic tubing and glass tubing are acceptable. To assure that the composite tubing 93 is effectively bendably flexible, the OD of the inner tubing 93a should be no greater than approximately 2 mm, and the wall thickness thereof no greater than approximately 0.5 mm, larger sizes being too stiff for conventionally necessary or desirably practical bending application of the tube connecting sets 91 as IV feeding connecting tubes, which is a conventional use for the tube connecting sets 91. The inner tubing sizes employed in the illustrative examples herein for the range of various practically encountered flow rate requirements and syringe sizes being of the order of 0.5 mm OD or less and 0.1 mm wall thickness or less, ample effectively bendable flexibility for the tube connecting sets 91 is provided.

Illustrative examples of variations in flow rate attainable by ±6-inch variations from a 36-inch nominal length of various different nominal ID tubing are shown in the following Table II, together with maximum and minimum ID tolerance variations which would result in necessity for ±6-inch tube length variations to accommodate these maximum and minimum ID variations. This Table II also indicates the maximum and minimum commercial tolerance variations of tubing ID for the respective nominal ID sizes, illustrating that normal commercial tolerance variations in tubing ID will not require greater than ±6-inch length variations.

health care professional, such as a pharmacist, may thus fill the syringe 71 with the prescribed dosage and concentration of the prescribed health care fluid to be administered to a patient and, based on this information and his own knowledge and/or the prescribing physician's order, he will thereupon select the appropriate flow rate tube connecting set from the assortment of interchangeably fittable differently metered tube connecting sets 191, 291, 391, etc., it being appreciated that additional selections of tube connecting sets greater than the illustrative three sets of the illustrative small assortment of FIG. 4 are desirably provided in order to enable the pharmacist to select and preset the precise flowrate required for a given need and fluid delivery assembly 101.

The tube connecting set selected from the assortment is then connected to the syringe 71 and cut-off valve 81, thereby providing a properly filled syringe 171 and preset metered flow rate tube connecting set for use as by a nurse or other suitably qualified health care personnel, after suitable expiration, to administer the fluid to a patient simply by inserting and securing the needle 11 to a patient and opening the valve 81, thereby minimizing the likelihood of inadvertent mistakes in dosage, concentration, content or rate of delivery of the prescribed health care fluid to a patient. The filled syringe 71, with cut-off valve 81 in closed position, may be loaded into

TABLE II

| Flow & ml/hr | Seconds to flow 36" | 36" Length Nominal ID uM | 36" Length ID Vol. cm³ × 10⁻⁴ | 30" Length ID uM | 30" Length Δ % | 42" Length ID uM | 42" Length Δ % | Max/Min Tolerance ΔID (uM) for ± 6" ΔL | Max/Min Commercial Tolerance ΔID (uM) from Nominal |
|---|---|---|---|---|---|---|---|---|---|
| 0.1 | 167.0 | 80.39 | 46.4 | 76.81 | 4.46 | 83.55 | 3.93 | +3.2 / −3.6 | ±3 |
| 1.0 | 52.8 | 142.96 | 146.8 | 136.59 | 4.46 | 148.57 | 3.93 | +5.61 / −6.37 | ±6 |
| 1.25 | 47.3 | 151.16 | 164.1 | 144.42 | 4.46 | 157.10 | 3.93 | +5.94 / −6.74 | ±6 |
| 2.0 | 37.4 | 170.00 | 207.55 | 162.42 | 4.46 | 176.68 | 3.93 | +6.68 / −7.58 | ±6 |
| 5.0 | 23.6 | 213.77 | 328.2 | 204.24 | 4.46 | 222.17 | 3.93 | +8.40 / −9.53 | ±12 |
| 10.0 | 16.7 | 254.22 | 464.1 | 242.89 | 4.46 | 264.21 | 3.93 | +9.99 / −11.33 | ±12 |
| 20.0 | 11.8 | 302.23 | 656.0 | 288.76 | 4.46 | 314.10 | 3.93 | +11.87 / −13.47 | ±12 |
| 30.0 | 9.6 | 334.57 | 803.9 | 319.66 | 4.46 | 347.71 | 3.93 | +13.14 / −14.91 | ±12 |
| 60.0 | 6.8 | 397.87 | 1136.9 | 380.14 | 4.46 | 413.50 | 3.93 | +15.63 / −17.73 | ±12 |
| 90.0 | 5.6 | 440.32 | 1390.4 | 420.70 | 4.46 | 457.62 | 3.93 | +17.30 / −19.62 | ±12 |

According to the invention, an assortment of tube connecting sets 191, 291, 391 may be made and supplied for use by a health care professional, the assortment including assorted different ID and flow rate connecting sets 191, 291, 391 (see FIG. 4 and enlarged cross section views in FIGS. 5-7) all of which have a tubing 193 outer diameter, e.g. 1/16-inch, formed by a respective plastic outer overcoat layer 193b, 293b, 393b and all of which have interchangeably usable Luer connectors 97, 99 on their opposite ends. Each different flow rate size tube connecting set, with its respectively appropriately-sized inner tube ID and cut tubing length, may be suitably indicated by color or other indicia in and/or on the respective tubing overcoat layer 193b, 293b, 393b thereby providing distinctive indicia in association therewith to enable a health care professional to determine its respective flow rate rating. A single responsible syringe holder/driver 13 either prior to or after attachment of the selected tube connecting set 91 to the cut-off valve 81.

FIGS. 8 and 9 illustrate plastic-overcoated tubing 493 and 593 for tube connecting sets according to the invention, having respectively plastic and glass inner fluid-path-forming tubing 493a and 593a, the respective outer plastic overcoat layers 493b and 593b being of a single common diameter, as previously described for the previously described embodiments.

While the invention has been described with respect to various illustrative embodiments, it will be apparent to one skilled in the art that various modifications and improvements may be made without departing from the scope and spirit of the invention. Accordingly, the invention is not to be limited by the illustrative embodiments, but only by the scope of the appended claims.

I claim:

1. A kit arrangement for delivering a fixed predetermined rate of flow of a selected fluid to a patient comprising:

a syringe having a body with a fluid discharge opening therein and a plunger slidable in said body to discharge fluid through said discharge opening, constant force driver means connectable to said syringe for exerting a constant discharge-effecting relative motion between said syringe plunger and said syringe body, and an assortment of tube connecting sets for selective connection of said syringe body discharge opening to a patient for delivery of fluid thereto from said syringe body, each of which tube connecting sets has the additional dual function of forming a fixed flow rate fluid metering means, each of said tube connecting sets of said assortment being formed of a flexible tubing section having a bore of substantially constant cross section size along its length and being substantially larger in cross-section than any particle which might occur in a medical fluid to be delivered therethrough, so as to enable said tubing section to form a predetermined fixed flow rate fluid metering means which is fully operational without need for a filter, said assortment of tube connecting sets including a plurality of tube connecting sets each of which itself forms a combined flexible tube connecting set and predetermined fixed flow rate metering means and provides a different one of a plurality of desired metered flow rates for a given syringe discharge pressure and fluid viscosity, and connecting fittings formed on opposite ends of each of said tube connecting sets to enable connection of any selected one of said assortment of tube connecting sets between said syringe body discharge opening and a patient to whom delivery of fluid is desired to be effected, the respective said flexible tubing section of each of said plurality of tube connecting sets having a length relative to the combination of its bore size, the viscosity of fluid desired to be delivered therethrough, and the fluid discharge pressure exerted at said syringe body discharge opening during effective fluid-discharge-effecting application of said constant force driver means to said syringe, which according to Poiseuille's Law will effect a single selected flow rate through the respective said flexible tubing section, whereby a health professional may select and use from said assortment any one of said plurality of tube connecting sets from said assortment for connection between said syringe and a patient to effect the corresponding predetermined fixed flow rate of delivery of a said desired fluid to a patient, the tubing section of each of said tube connecting sets of said assortment including an outer circumferential overcoat layer of plastic formed over an inner tubing section, said assortment including a plurality of tube connecting sets whose respective said inner tubing sections are of different outer diameter as well as different inner diameter, said outer overcoat layer for all of said tube connector sets being of substantially the same outer peripheral size along its length, independent of the inner bore size and/or outer peripheral size of the various respective inner tubing sections of such tube connector sets, to thereby accommodate and accept end connecting fittings of a tube connecting bore size common to all of said tube connecting sets independent of the inner bore size and flow rate of any given tube connecting set of said assortment.

2. An arrangement according to claim 1, said inner flexible tubing section being formed of plastic tubing.

3. An arrangement according to claim 1, said inner flexible tubing section being formed of thin-walled glass tubing.

4. An arrangement according to claim 1, said inner flexible tubing section being formed of metal.

5. An arrangement according to claim 1, each of said tube connecting sets having identifying indicia in association therewith to enable determination by a health professional of its respective fixed metered flow rate rating of said given syringe discharge pressure and fluid viscosity.

6. An arrangement according to claim 5, said indicia being formed on the respective said outer overcoat layer of each respective said tube connecting set.

7. An arrangement according to claim 5, said indicia being a respective color indicia for each respective flow rate rating.

8. A kit assortment of tube connecting sets for selective connection of a substantially constant-force-driven syringe to a patient for delivery of fluid thereto from said syringe body, each of which tube connecting sets has the additional dual function of forming a fixed flow rate fluid metering means, each of said tube connecting sets of said assortment being formed of a flexible tubing section having a bore of substantially constant cross-section size along its length which bore is very small compared to its length and which taken over its entire length forms a substantial and effective predetermined flow-rate-restrictive metering means for administering medical fluids therethrough, and said bore being further substantially larger in cross-section than any particle which might occur in a medical fluid to be delivered therethrough, so as to enable said tubing section to form a predetermined fixed flow rate fluid metering means which is fully operational without need for a filter, said kit assortment of tube connecting sets including a plurality of tube connecting sets each of which itself forms a combined flexible tube connecting set and predetermined fixed flow rate metering means and provides a different one of a plurality of desired metered flow rates for a given syringe discharge pressure and fluid viscosity, and end connecting fittings formed on opposite ends of each of said tube connecting sets to enable connection of any selected one of said assortment of tube connecting sets between a syringe and a patient to whom delivery of fluid is desired to be effected, the respective said flexible tubing section of each of said plurality of tube connecting sets having a length relative to the combination of its bore size, the viscosity of fluid desired to be delivered therethrough, and the fluid discharge pressure exerted by a constant-force-driven syringe to which a selected one of said tube connecting sets is to be connected, which according to Poiseuille's Law will effect a single selected flow rate through the respective said flexible tubing section, whereby a health professional may select and use from said assortment any one of said plurality of tube connecting sets from said assortment for connection between a said substantially constant-force-driven syringe and a patient to effect the corresponding predetermined fixed flow rate of delivery of a said selected one of said plurality of tube connecting sets from said assortment, the flexible tubing section of each of said tube connecting sets of said assortment including an outer overcoat layer of plastic formed over an inner flexible tubing section, said outer overcoat layer for all of said tube connector sets being of effectively substantially the same outer peripheral size along its length, independent of the inner and/or outer peripheral size of the various inner flexible plastic tubing of such tube connector sets.

9. An arrangement according to claim 8, said inner flexible tubing section being formed of plastic tubing.

10. An arrangement according to claim 8, said inner flexible tubing section being formed of thin-walled glass tubing.

11. An arrangement according to claim 8, said inner flexible tubing section being formed of metal.

12. An arrangement according to claim 8, each of said tube connecting sets having identifying indicia in association therewith to enable determination by a health professional of its respective fixed metered flow rate rating for said given syringe discharge pressure and fluid viscosity.

13. An arrangement according to claim 12, said indicia being formed on the respective said outer overcoat layer of each respective said tube connecting set.

14. An arrangement according to claim 12, said indicia being a respective distinctive color indicia indicative of each respective flow rate rating.

* * * * *